US011963882B2

(12) United States Patent
Bohenick et al.

(10) Patent No.: US 11,963,882 B2
(45) Date of Patent: Apr. 23, 2024

(54) MAMMALIAN BONY ANCHOR

(71) Applicant: Osseus Fusion Systems, Dallas, TX (US)

(72) Inventors: John Bohenick, Troy, MI (US); Chase D. Tipping, Dallas, TX (US); Kyle Blaskovich, Dallas, TX (US); Andrew Schindler, Dallas, TX (US)

(*) Notice: Subject to any disclaimer, the term of this patent is extended or adjusted under 35 U.S.C. 154(b) by 0 days.

(21) Appl. No.: 17/665,373

(22) Filed: Feb. 4, 2022

(65) Prior Publication Data
US 2023/0248532 A1 Aug. 10, 2023

(51) Int. Cl.
A61F 2/44 (2006.01)
A61F 2/30 (2006.01)
A61F 2/46 (2006.01)

(52) U.S. Cl.
CPC ............ A61F 2/4455 (2013.01); A61F 2/442 (2013.01); A61F 2002/30331 (2013.01); A61F 2002/30774 (2013.01); A61F 2002/4629 (2013.01)

(58) Field of Classification Search
CPC ............... A61F 2/4455; A61F 2/442; A61F 2002/30331; A61F 2002/30774; A61F 2002/4629
See application file for complete search history.

(56) References Cited

U.S. PATENT DOCUMENTS

| | | | |
|---|---|---|---|
| 9,872,780 B2 * | 1/2018 | Reed | A61F 2/4611 |
| 11,413,151 B1 * | 8/2022 | McIver | A61F 2/442 |
| 2009/0105832 A1 * | 4/2009 | Allain | A61F 2/4465 623/17.11 |
| 2011/0230971 A1 * | 9/2011 | Donner | A61F 2/442 606/246 |
| 2013/0150968 A1 * | 6/2013 | Dinville | A61F 2/46 623/17.16 |
| 2015/0305887 A1 * | 10/2015 | McAtamney | A61F 2/4611 623/17.16 |
| 2016/0151171 A1 * | 6/2016 | Mozeleski | A61B 17/80 623/17.16 |
| 2019/0000637 A1 * | 1/2019 | Gilbride | A61B 17/8685 |
| 2021/0059834 A1 * | 3/2021 | Miguel | A61F 2/30749 |

* cited by examiner

Primary Examiner — Nicholas J Plionis
(74) Attorney, Agent, or Firm — Merle W Richman, III

(57) ABSTRACT

Embodiments of mammalian bony anchor(s) 10 for treating mammalian bony segments such as in conjunction with other system(s) to encourage bony fusion, stabilize, maintain spacing between, or couple the bony segments. Other embodiments may be described and claimed.

19 Claims, 8 Drawing Sheets

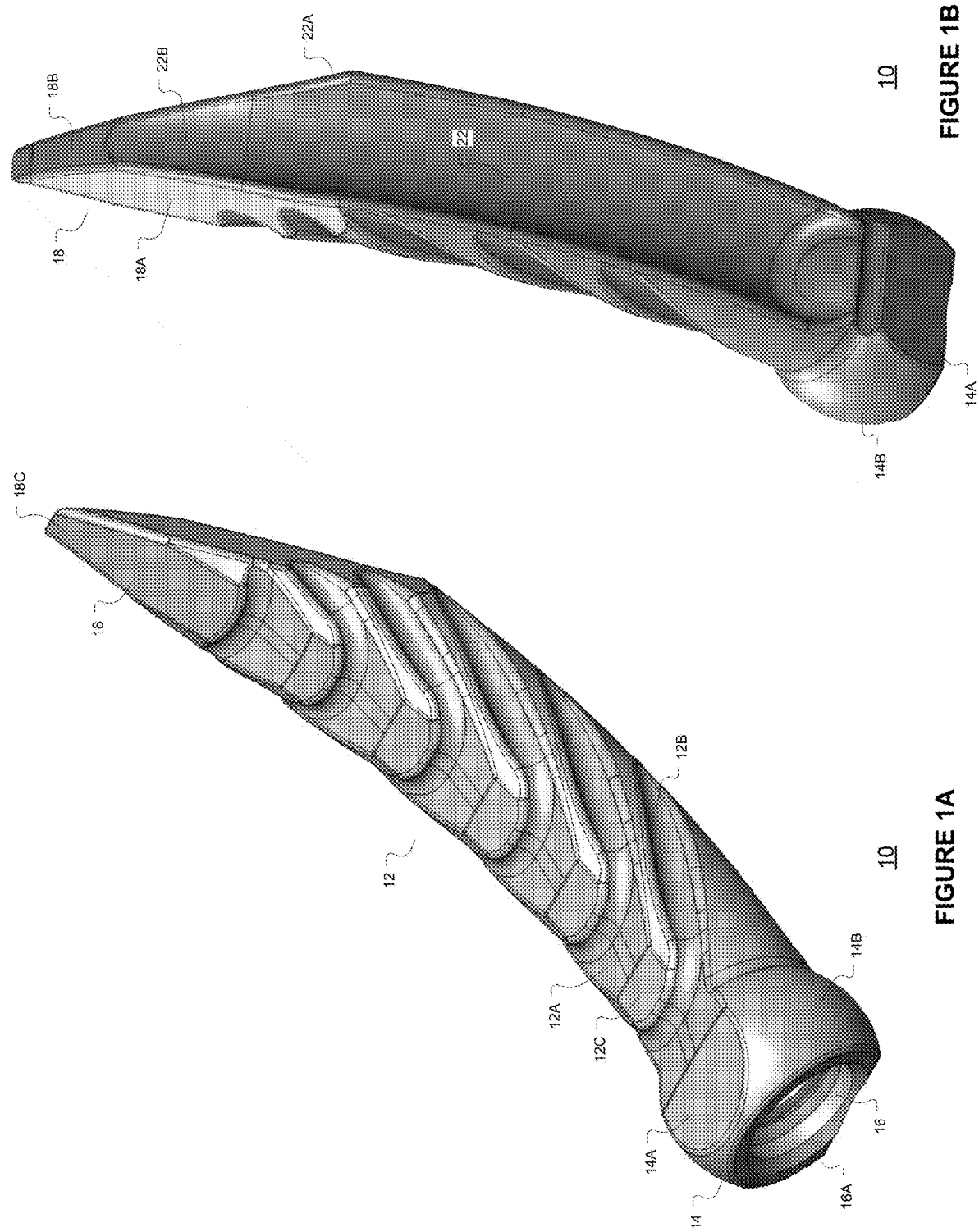

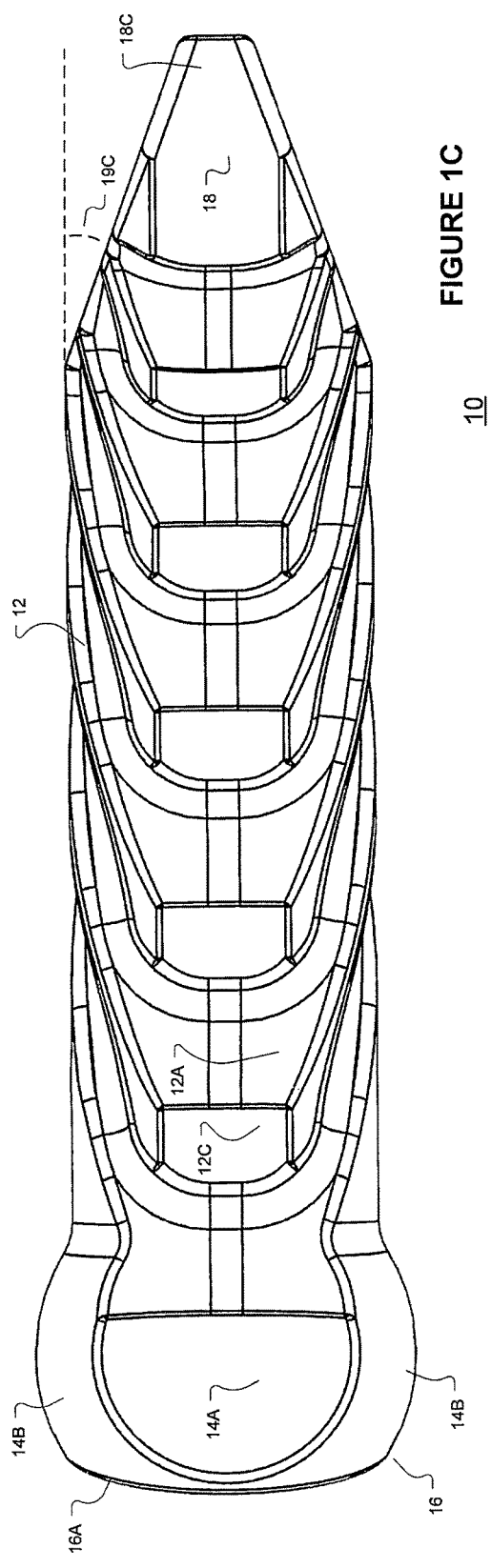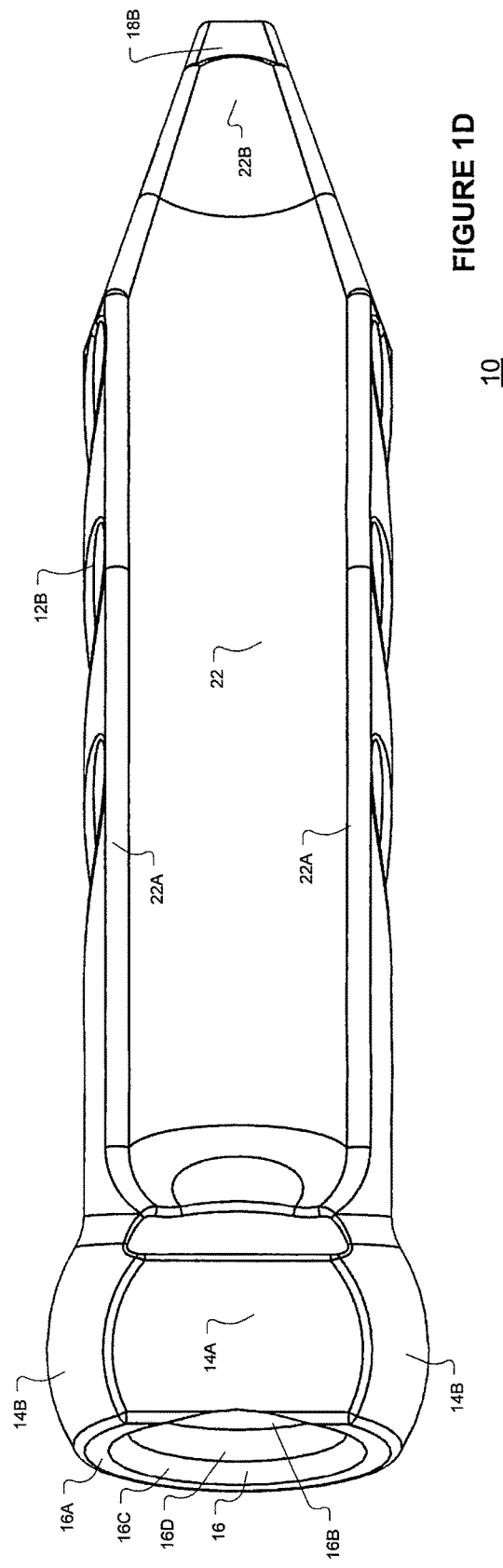

30

30

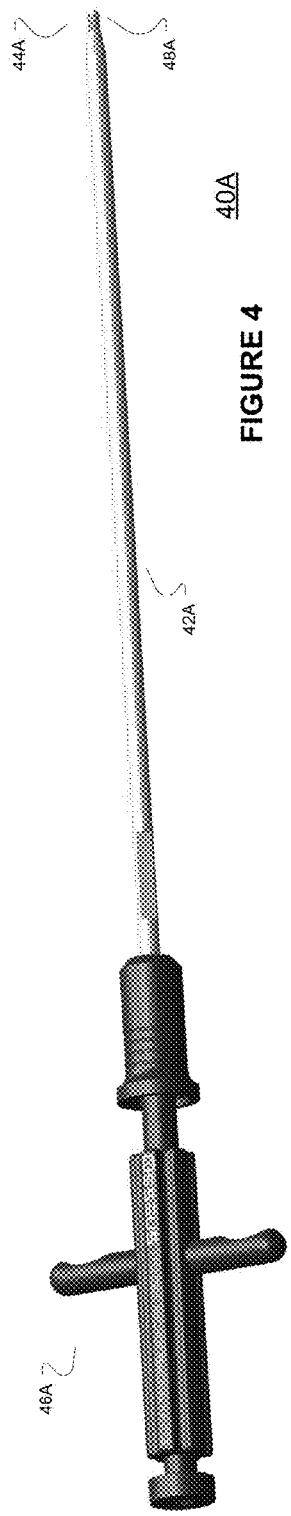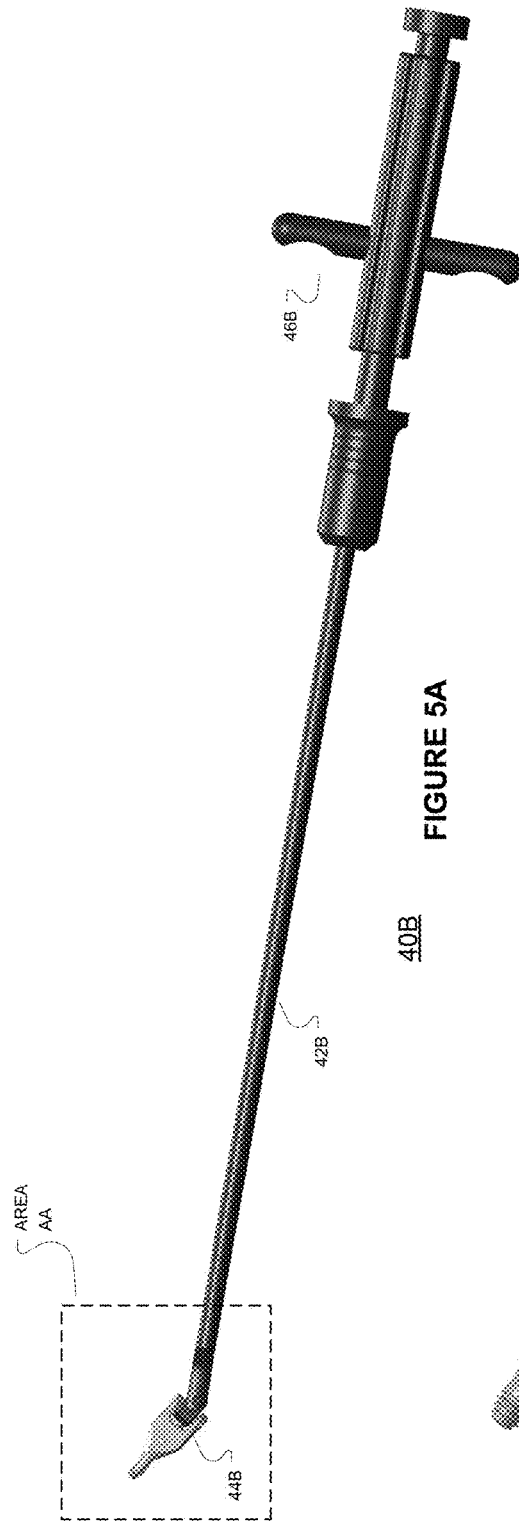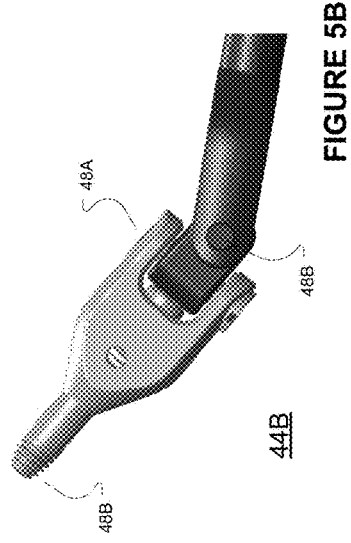

MAMMALIAN BONY ANCHOR

TECHNICAL FIELD

Various embodiments described herein relate generally to treating mammalian bony segments, including systems and methods that employ anchors to stabilize, maintain spacing between, or couple one or more mammalian bony segments.

BACKGROUND INFORMATION

It may be desirable to treat one or more bony segments via mammalian bony anchor(s) such as in conjunction with other system(s) to encourage bony fusion, stabilize, maintain spacing between, or couple the bony segments, the present invention provides such mammalian bony anchor(s).

BRIEF DESCRIPTION OF THE DRAWINGS

FIG. 1A is a simplified isometric front drawing of a mammalian bony anchor according to various embodiments.

FIG. 1B is a simplified isometric rear drawing of a mammalian bony anchor according to various embodiments.

FIG. 1C is a simplified top view of a mammalian bony anchor according to various embodiments.

FIG. 1D is a simplified bottom view of a mammalian bony anchor according to various embodiments.

FIG. 4 is a simplified side view of straight-line removal tool for a mammalian bony anchor according to various embodiments.

FIG. 5A is a simplified side view of variable-angle removal tool for a mammalian bony anchor according to various embodiments.

FIG. 5B is a simplified enlarged view of area AA of the variable-angle removal tool for a mammalian bony anchor shown in FIG. 5A.

DETAILED DESCRIPTION

Figure 1E:
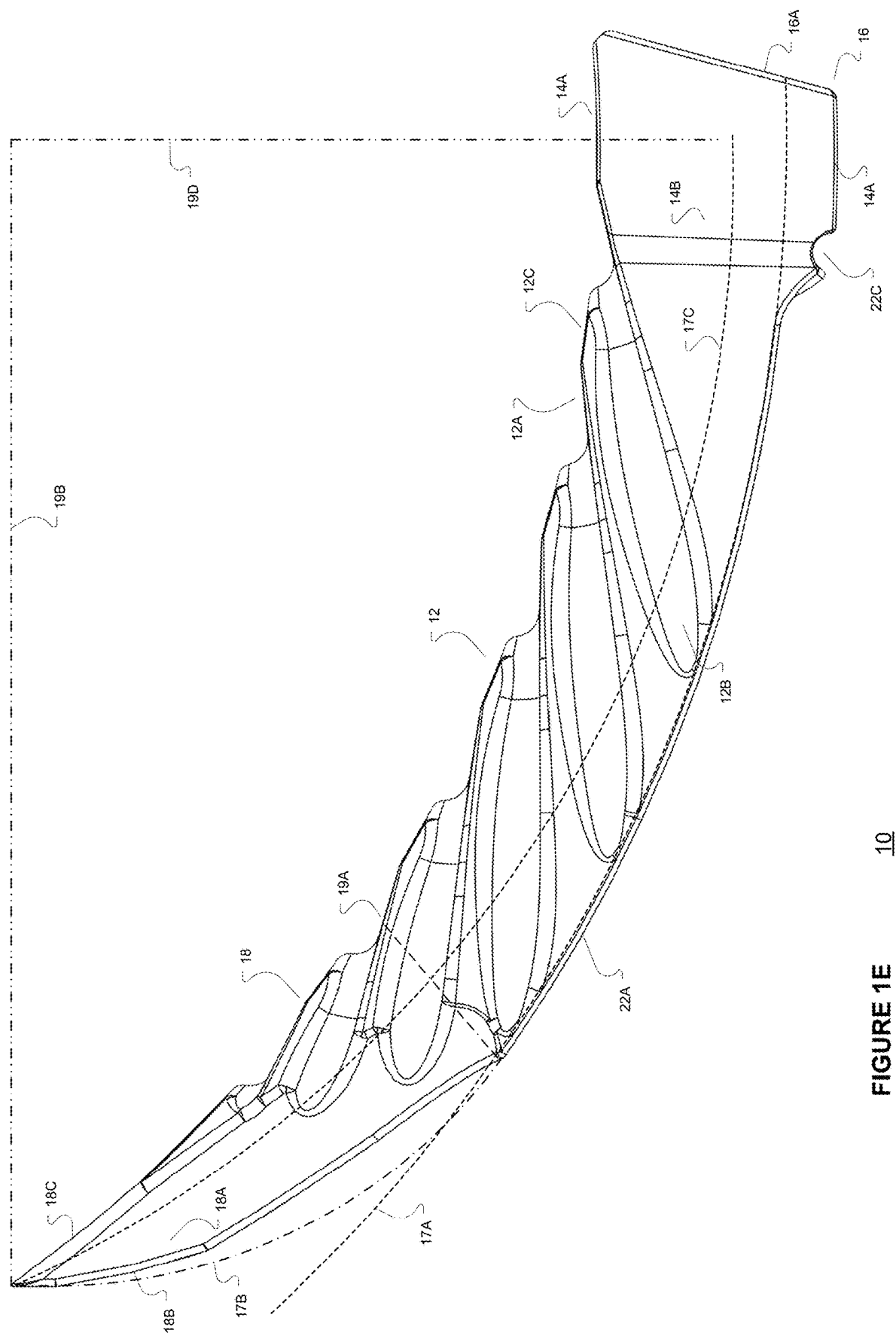
FIG. 1E is a simplified left side view of a mammalian bony anchor according to various embodiments.
Figure 1G:
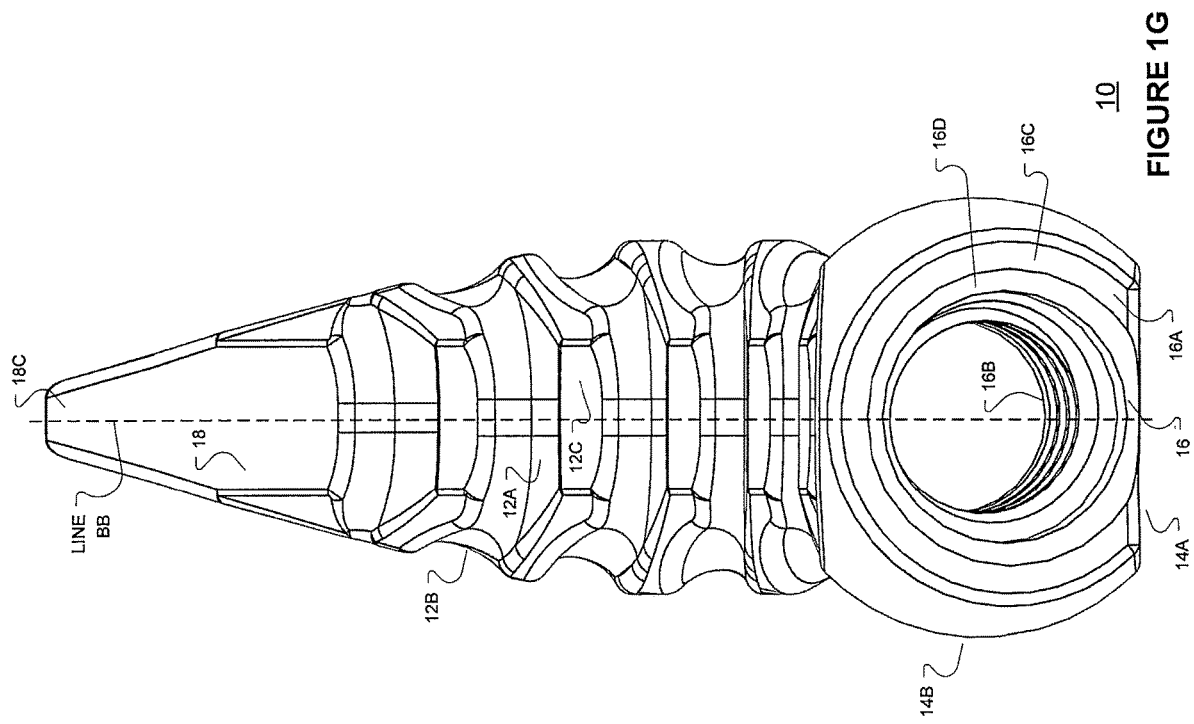
FIG. 1G is a simplified rear view of a mammalian bony anchor according to various embodiments.
Figure 1F:
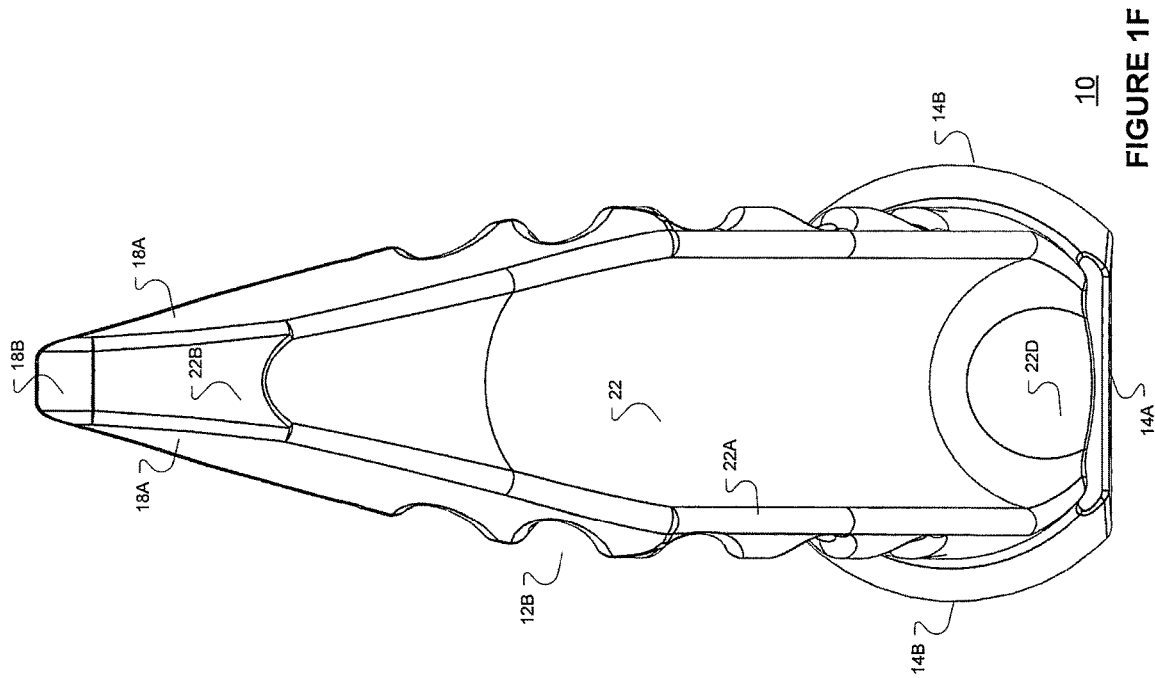
FIG. 1F is a simplified bottom front view of a mammalian bony anchor according to various embodiments.
Figure 6B:
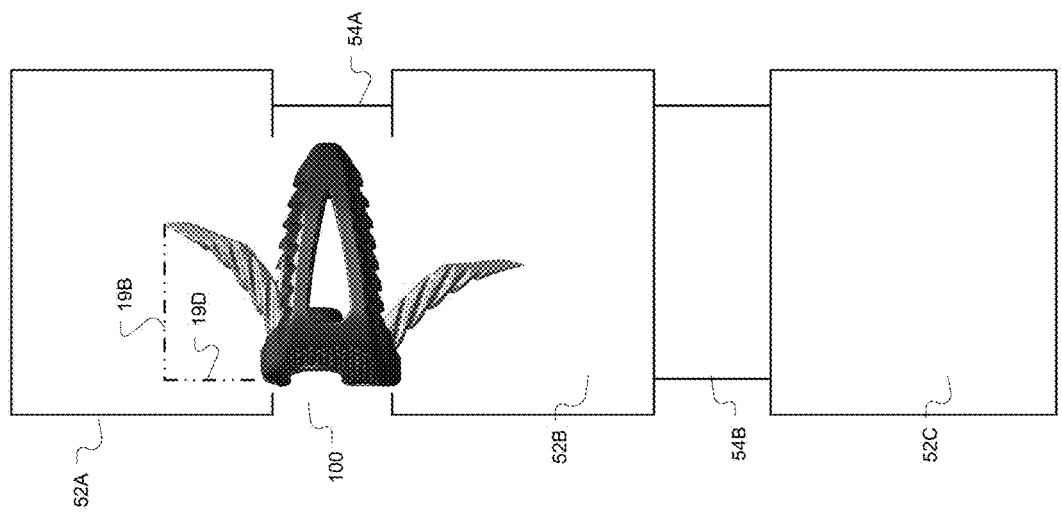
FIG. 6B is a left side view of an adjacent mammalian bony segments fixation system including an implant and a plurality of mammalian bony anchors operatively inserted between a center bony segment and an adjacent upper bony segment according to various embodiments.
Figure 6A:
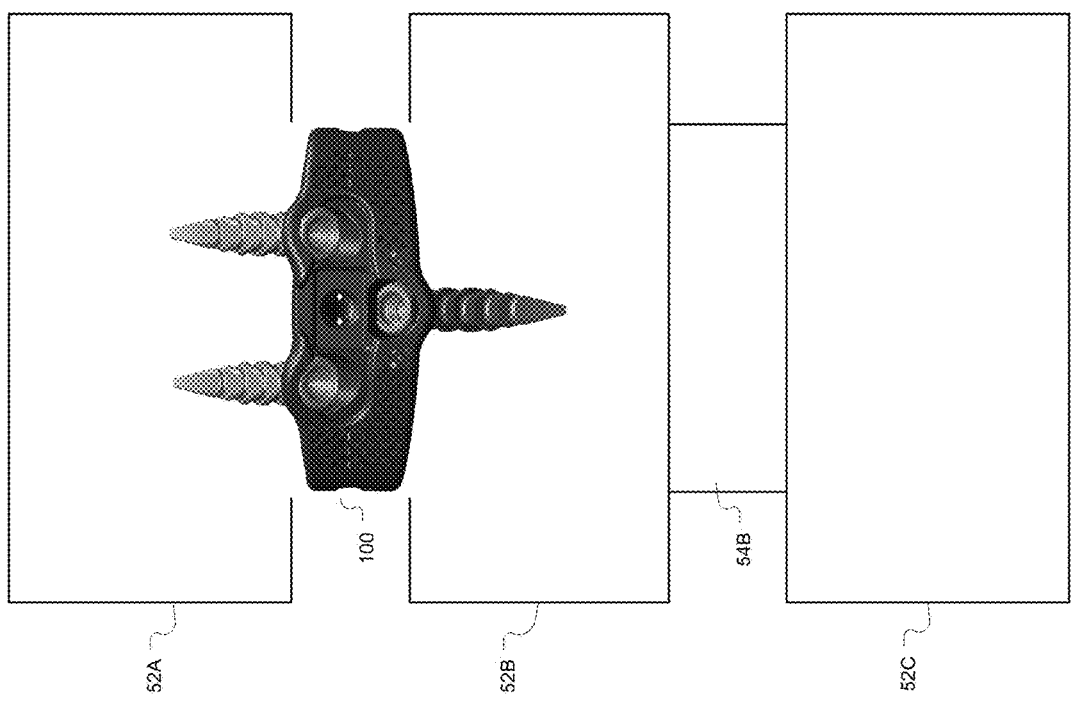
FIG. 6A is a posterior view of an adjacent mammalian bony segments fixation system including an implant and a plurality of mammalian bony anchors operatively inserted between a center bony segment and an adjacent upper bony segment according to various embodiments.

It may be desirable to treat one or more bony segments 52A-C via mammalian bony anchor(s) 10 such as in conjunction with other system(s) 30 to encourage bony fusion, stabilize, maintain spacing between, or couple the bony segments 52A-C(FIGS. 6A-6B). FIG. 1A is a simplified isometric front drawing of a mammalian bony anchor 10 according to various embodiments. FIG. 1B is a simplified isometric rear drawing of the mammalian bony anchor 10 according to various embodiments. FIG. 1C is a simplified top view of the mammalian bony anchor 10 according to various embodiments. FIG. 1D is a simplified bottom view of the mammalian bony anchor 10 according to various embodiments. FIG. 1E is a simplified left side view of the mammalian bony anchor 10 according to various, embodiments. FIG. 1F is a simplified bottom front view of the mammalian bony anchor according to various embodiments. FIG. 1G is a simplified rear view of the mammalian bony anchor 10 according to various embodiments.

As shown in FIGS. 1A-1G, the mammalian bony anchor (MBA) 10 includes a shaft 12, a base section 14, a tool interface 16, and a tapered extended tip section 18. As shown in FIGS. 1E and 1H, the MBA 10 may have an arcuate shape with a primary radius 17A for the base section 12, a first, secondary radius 17B for the tip section 18 where the radius 17A is larger than the radius 17B, and a third, tertiary radius 17D for the tip edge 18C. In an embodiment, the radius 17A may be about 1.5 to 2.5 times larger than radius 17B and about 1.75 to 2.0 times larger in an embodiment, 2.0 to 3.0 times larger than radius 17D. As shown in FIGS. 1E and 6B, the MBA 10 may have an effective depth of insertion 19B which is less than the overall length 17C the MBA 10. The MBA 10 may also have a height 19D where the length of the effective hypotenuse formed by 19B and 19D (square root of the sum of the squares of the 19B and 19D) is less than the overall length 17C of the BMA 10.

As shown in FIGS. 1A-1G, the shaft section 12 and tip section 18 may include a plurality of shelves or scallops 12A. Each scallop 12A may include a flat ledge 12C and an undercut 12B. The flat ledge 12C may ease insertion of the MBA 10 into a bony segment 52A-C while the remainder of each scallop 12A including the edge around the undercut 12B may help prevent expulsion of the MBA 10 once inserted into a desired position in a bony segment 52A-C.

As also shown in FIGS. 1A-1G, the tip section 18 may also include a large flat region 18C on the top, flat portions 18A on the sides, and a smaller flat region 18B on the bottom that may also ease insertion of the MBA 10 into a bony segment 52A-C. As also shown in FIGS. 1A-1G, the tip section 18 may have a narrower tip where the sides 18A may form an angle (19C in FIG. 1C) of about 20 to 60 degrees and about 40 degrees in an embodiment. As also shown in FIGS. 1A-1G, the bottom 22 of the MBA 10 may be partially cylindrical in relief, with smaller sections 22B in the tip section 18 than the sections 22A of the rear in the shaft section 12. The shape of the rear 22 may also reduce the force required to inset the MBA 10 into a desired position in a bony segment 52A-C.

Figure 2:
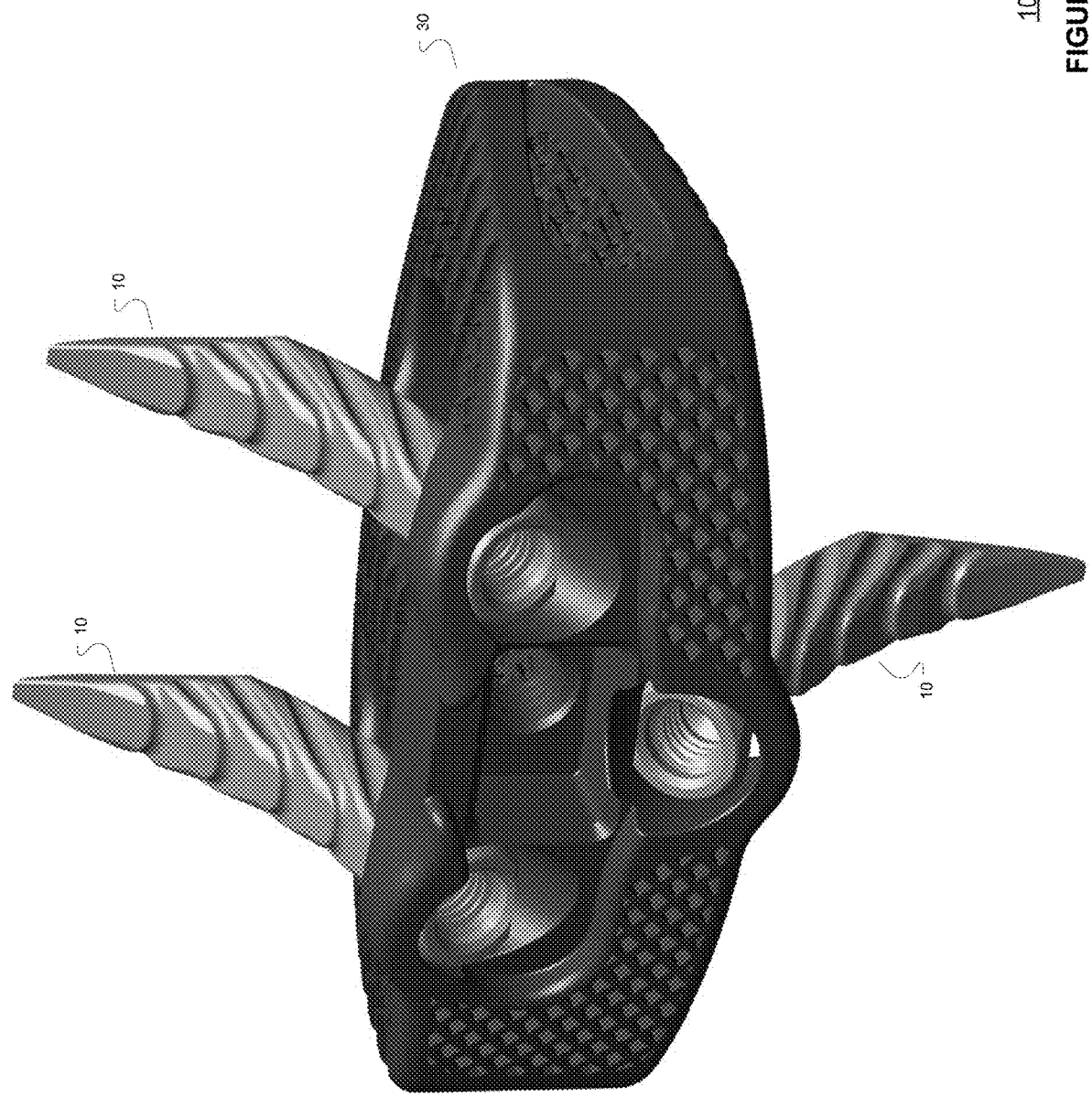
FIG. 2 is a simplified isometric view of an adjacent mammalian bony segments fixation system including an implant and a plurality of mammalian bony anchors according to various embodiments.
Figure 3A:
FIG. 3A is a simplified isometric front drawing of adjacent mammalian bony segments implant according to various embodiments.
Figure 3B:
FIG. 3B is a simplified front drawing of adjacent mammalian bony segments implant according to various embodiments.

In an embodiment, an MBA 10 may be inserted into a desired position in a bony segment 52A-C via an impaction tool that acts on the tool interface 16 flat impact surface 16A due to its configuration/geometry. As shown FIGS. 1A-1G, the tool interface 16 may include an internal threaded section 16B sized to receive a removal tool interface's external thread 48A, 48B as shown in FIGS. 4-5B. The tool interface 16 may also include a chamfer 16C and counterbore 16D each having a diameter greater than the internal threads 16B. The base 14 may have a flat top and bottom section 14A and partially spherical sides 14B. This base 14 configuration enables the MBA 10 to have a large range of pivotability when used in conjunction with an implant 30 such as shown in FIGS. 2-3B. As shown in FIGS. 3A-3B, an implant 30 may include a plurality of bone anchor interfaces 32 that are spherical in relief and enable the MBA 10 base 14 section to pivot over a large range.

As shown in FIG. 2, when coupled to an implant, an MBA 10 may form about a 90-degree angle at its tip section 18 relative to the implant 30. When inserted between bony sections 52A-52B as shown in FIGS. 6A and 6B, the MBA 10 may provide substantial retention and anti-expulsion force with the bony segments 52A-B. In an embodiment, the bony segments 52A-C may be vertebrae with disc nucleus 54A-B located between adjacent vertebrae 52A, 52B or 52B, 52C. In an embodiment, the vertebrae 52A-C may be lumbar vertebrae and the system 100 including implant 30 and plurality of MBA 10 (two MBA 10 engaging upper bony segment and one MBA 10 engaging the lower, adjacent bony segment) may be configured for insertion from an anterior position (part an anterior lumbar interior fusion (ALIF)) construct.

When necessary to remove an inserted MBA 10, it may be ideally moved along the arc of the shaft 12 radius 17A shown in FIG. 1E. The removal tools 40A, 40B shown in FIGS. 4-5B may be coupled to an inserted MBA 10 via the tool's interface threads 48A, 48B to an inserted MBA 10 tool interface 16 internal threads 16B and be guided to the threads via the chamfer 16C and counterbore 16D. The tools 40A, B may then be used to remove an inserted MBA 10 at or near the arc 17A via the shafts 42A, 42B and handles 46A, 46B. As shown in FIG. 5B the tool 40B may be pivotable about two different axes 48A, 48B to ease the attachment to an inserted MBA 10 to be removed along the arc or radius 17A.

As noted, the geometry of the MBA 10 may provide greater expulsion strength and reliable cortical vertebral endplate penetration when inserted into vertebra 52A-C. In an embodiment, the MBA 10 outer surface may have scaling to provided increased osteointegration. The MBA 10 scallops 12A and undercuts 12B may also grip bone when inserted into thereto. The MBA 10 tip 18 structure may enable it to reliably penetrate cortical vertebral endplates without causing nor incurring fracture damage when be inserted into a vertebra 52A-C. In an embodiment, the MBA 10 may provide various fixation angles, convergent and/or divergent. In an embodiment, the MBA 10 and implant 30 may be formed of a biocompatible, substantially radiolucent material or complex of materials.

In an embodiment, the implant 30 may be formed of a polymer, ceramic, or combination of both, including Polyether ether ketone (PEEK) or other member of the polyaryletherketone family. The MBA 10 may be formed of a metal, alloy, or other osteoconductive material. In an embodiment, the MBA 10 may be formed from Titanium.

The accompanying drawings that form a part hereof show, by way of illustration and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The Abstract of the Disclosure is provided to comply with 37 C.F.R. § 1.72(b), requiring an abstract that will allow the reader to quickly ascertain the nature of the technical disclosure. It is submitted with the understanding that it will not be used to interpret or limit the scope or meaning of the claims. In the foregoing Detailed Description, various features are grouped together in a single embodiment for the purpose of streamlining the disclosure. This method of disclosure is not to be interpreted to require more features than are expressly recited in each claim. Rather, inventive subject matter may be found in less than all features of a single disclosed embodiment. Thus, the following claims are hereby incorporated into the Detailed Description, with each claim standing on its own as a separate embodiment.

What is claimed is:

1. A mammalian bony anchor (MBA) for insertion into a bony segment including:
   an arcuate shaft section having a first length and effective first radius along its length;
   an arcuate tip section having a second length and an effective second radius along its length; and
   an arcuate tip edge having an effective third radius along its length,
   wherein the effective first radius is greater than the effective second radius, the first length is greater than the second length, and the effective second radius is greater than the effective third radius,
   wherein the arcuate shaft section has an at least partially cylindrical recess on its bottom side.

2. The MBA for insertion into a bony segment of claim 1, wherein the arcuate shaft section includes a base with a tool interface at the base proximal end and the tool interface includes an impaction surface.

3. The MBA for insertion into a bony segment of claim 2, wherein the impaction surface is at an angle relative to the normal of the effective first radius of the arcuate shaft section.

4. The MBA for insertion into a bony segment of claim 2, wherein the tool interface includes an opening with internal threads.

5. The MBA for insertion into a bony segment of claim 2, wherein the tool interface includes an opening with a counterbore followed by internal threads.

6. The MBA for insertion into a bony segment of claim 5, wherein the tool internal threads are configured to be coupled to a removal tool.

7. The MBA for insertion into a bony segment of claim 2, wherein the tool interface includes an opening with a chamfer and a counterbore followed by internal threads.

8. The MBA for insertion into a bony segment of claim 7, wherein the tool internal threads are configured to be coupled to a removal tool.

9. The MBA for insertion into a bony segment of claim 1, wherein the arcuate tip section is tapered.

10. The MBA for insertion into a bony segment of claim 1, wherein the arcuate shaft section is at least partially cylindrical on its top side.

11. The MBA for insertion into a bony segment of claim 1, wherein the arcuate tip section includes at least one shelve on its top side.

12. The MBA for insertion into a bony segment of claim 11, wherein the arcuate shaft section includes a plurality of shelves on its top side.

13. The MBA for insertion into a bony segment of claim 11, wherein each shelve includes a flat ledge and an undercut to help prevent expulsion.

14. The MBA for insertion into a bony segment of claim 1, wherein the arcuate tip section includes a flat top side and angled, flat side portions forming a narrow tip.

15. The MBA for insertion into a bony segment of claim 1, wherein the arcuate tip section includes a flat top side, a flat side section, and angled, flat side portions forming a narrow tip.

16. The MBA for insertion into a bony segment of claim 15, wherein the arcuate tip section is at least partially cylindrical on its top side.

17. The MBA for insertion into a bony segment of claim 16, the arcuate tip section is at least partially cylindrical in relief on its bottom side.

18. The MBA for insertion into a bony segment of claim 1, wherein the arcuate tip section is at least partially cylindrical on its top side.

19. The MBA for insertion into a bony segment of claim 18, wherein the arcuate tip section is at least partially cylindrical in relief on its bottom side.

\* \* \* \* \*